United States Patent
Shalyt et al.

(10) Patent No.: US 7,186,326 B2
(45) Date of Patent: Mar. 6, 2007

(54) EFFICIENT ANALYSIS OF ORGANIC ADDITIVES IN AN ACID COPPER PLATING BATH

(75) Inventors: Eugene Shalyt, Washington Township, NJ (US); Michael Pavlov, Fairlawn, NJ (US); Peter Bratin, Flushing, NY (US); Alex Kogan, Carlstadt, NJ (US); Michael James Perpich, Hackensack, NJ (US)

(73) Assignee: ECI Technology, Inc.

( * ) Notice: Subject to any disclaimer, the term of this patent is extended or adjusted under 35 U.S.C. 154(b) by 344 days.

(21) Appl. No.: 10/856,619

(22) Filed: May 27, 2004

(65) Prior Publication Data

US 2005/0263399 A1    Dec. 1, 2005

(51) Int. Cl.
*C25D 21/14* (2006.01)
*G01N 27/26* (2006.01)
(52) U.S. Cl. .......................... 205/81; 205/101; 205/787
(58) Field of Classification Search ................... 205/81, 205/82, 101, 787
See application file for complete search history.

(56) References Cited

U.S. PATENT DOCUMENTS 6,280,602 B1 * 8/2001 Robertson .................... 205/775
6,572,753 B2 * 6/2003 Chalyt et al. .................. 205/81

* cited by examiner

*Primary Examiner*—Roy King
*Assistant Examiner*—William T. Leader
(74) *Attorney, Agent, or Firm*—D. Morgan Tench

(57) ABSTRACT

Suppressor and anti-suppressor additives in an acid copper sulfate plating bath are analyzed by the cyclic voltammetric stripping (CVS) method without cleaning or rinsing the cell between the two analyses. The suppressor analysis is performed first and the suppressor concentration in the resulting measurement solution is adjusted to a predetermined value corresponding to full suppression. This fully-suppressed solution is then used as the background electrolyte for the anti-suppressor analysis. This integrated analysis approach provides results comparable to those obtained with cell cleaning and rinsing between the analyses but significantly reduces the analysis time, consumption of expensive chemicals, and quantity of hazardous waste generated.

20 Claims, 2 Drawing Sheets

EFFICIENT ANALYSIS OF ORGANIC ADDITIVES IN AN ACID COPPER PLATING BATH

BACKGROUND OF THE INVENTION

1. Field of the Invention

This invention is concerned with analysis of organic additives and contaminants in plating baths as a means of providing control over the deposit properties.

2. Description of the Related Art

Electroplating baths typically contain organic additives whose concentrations must be closely controlled in the low parts per million range in order to attain the desired deposit properties and morphology. One of the key functions of such additives is to level the deposit by suppressing the electrodeposition rate at protruding areas in the substrate surface and/or by accelerating the electrodeposition rate in recessed areas. Accelerated deposition may result from mass-transport-limited depletion of a suppressor additive species that is rapidly consumed in the electrodeposition process, or from accumulation of an accelerating species that is consumed with low efficiency. The most sensitive methods available for detecting leveling additives in plating baths involve electrochemical measurement of the metal electrodeposition rate under controlled hydrodynamic conditions for which the additive concentration in the vicinity of the electrode surface is well-defined.

Cyclic voltammetric stripping (CVS) analysis [D. Tench and C. Ogden, J. Electrochem. Soc. 125, 194 (1978)] is the most widely used bath additive control method and involves cycling the potential of an inert electrode (e.g., Pt) in a plating solution between fixed potential limits so that metal is alternately plated on and stripped from the electrode surface. Such potential cycling is designed to establish a steady state for the electrode surface so that reproducible results are obtained. Accumulation of organic films or other contaminants on the electrode surface can be avoided by periodically cycling the potential of the electrode in a plating solution without organic additives and, if necessary, polishing the electrode using a fine abrasive. Cyclic pulse voltammetric stripping (CPVS), also called cyclic step voltammetric stripping (CSVS), is a variation of the CVS method that employs discrete changes in potential during the analysis to condition the electrode so as to improve the measurement precision [D. Tench and J. White, J. Electrochem. Soc. 132, 831 (1985)]. A rotating disk electrode configuration is typically employed for both CVS and CPVS analysis to provide controlled hydrodynamic conditions.

For CVS and CPVS analyses, the metal deposition rate may be determined from the current or charge passed during metal electrodeposition but it is usually advantageous to measure the charge associated with anodic stripping of the metal from the electrode. A typical CVS/CPVS rate parameter is the stripping peak area ($A_r$) for a predetermined electrode rotation rate. The CVS method was first applied to control copper pyrophosphate baths (U.S. Pat. No. 4,132,605 to Tench and Ogden) but has since been adapted for control of a variety of other plating systems, including the acid copper sulfate baths that are widely used by the electronics industry [e.g., R. Haak, C. Ogden and D. Tench, Plating Surf. Fin. 68(4), 52 (1981) and Plating Surf. Fin. 69(3), 62 (1982)].

Acid copper sulfate electroplating baths require a minimum of two types of organic additives to provide deposits with satisfactory properties and good leveling characteristics. The suppressor additive (also called the "polymer", "carrier", or "wetter", depending on the bath supplier) is typically a polymeric organic species, e.g., high molecular weight polyethylene glycol or polypropylene glycol, which adsorbs strongly on the copper cathode surface to form a film that sharply increases the overpotential for copper deposition. This prevents uncontrolled copper plating that would result in powdery or nodular deposits. An anti-suppressor additive (also called the "brightener", "accelerator" or simply the "additive", depending on the bath supplier) is required to counter the suppressive effect of the suppressor and provide the accelerated deposition within substrate recesses needed for leveling. Plating bath vendors typically provide additive solutions that may contain additives of more than one type, as well as other organic and inorganic addition agents. The suppressor additive may be comprised of more than one chemical species and generally involves a range of molecular weights.

Acid copper sulfate baths have functioned well for plating the relatively large surface pads, through-holes and vias found on printed wiring boards (PWB's) and are currently being adapted for plating fine trenches and vias in dielectric material on semiconductor chips. The electronics industry is transitioning from aluminum to copper as the basic metallization for semiconductor integrated circuits (IC's) in order to increase device switching speed and enhance electromigration resistance. The leading technology for fabricating copper IC chips is the "Damascene" process (see, e.g., P. C. Andricacos, Electrochem. Soc. Interface, Spring 1999, p. 32; U.S. Pat. No. 4,789,648 to Chow et al.; U.S. Pat. No. 5,209,817 to Ahmad et al.), which depends on copper electroplating to provide complete filling of the fine features involved. The organic additives in the bath must be closely controlled since they provide the copper deposition rate differential required for bottom-up filling.

As the feature size for the Damascene process has shrunk below 0.2 μm, it has become necessary to utilize a third organic additive in the acid copper bath in order to avoid overplating the trenches and vias. Note that excess copper on Damascene plated wafers is typically removed by chemical mechanical polishing (CMP) but the copper layer must be uniform for the CMP process to be effective. The third additive is called the "leveler" (or "booster", depending on the bath supplier) and is typically an organic compound containing nitrogen or oxygen that also tends to decrease the copper plating rate. In order to attain good bottom-up filling and avoid overplating of ultra-fine chip features, the concentrations of all three additives must be accurately analyzed and controlled.

The suppressor, anti-suppressor and leveler concentrations in acid copper sulfate baths can all be determined by CVS analysis methods based on the effects that these additives exert on the copper electrodeposition rate. At the additive concentrations typically employed, the effect of the suppressor in reducing the copper deposition rate is usually much stronger than that of the leveler so that the concentration of the suppressor can be determined by the usual CVS response curve or dilution titration analysis [W. O. Freitag, C. Ogden, D. Tench and J. White, Plating Surf. Fin. 70(10), 55 (1983)]. Likewise, the anti-suppressor concentration can be determined by the linear approximation technique (LAT) or modified linear approximation technique (MLAT) described by R. Gluzman [Proc. 70$^{th}$ Am. Electroplaters Soc. Tech. Conf., Sur/Fin, Indianapolis, Ind. (June 1983)]. A method for measuring the leveler concentration in the presence of interference from both the suppressor and anti-suppressor is described in U.S. Pat. No. 6,572,753 to Chalyt et al.

CVS dilution titration analysis for the suppressor additive typically involves measurements of $A_r(0)$ for the plating bath supporting electrolyte (without organic additives) and $A_r$ values for a plurality of measurement solutions resulting from standard addition of the plating bath to the supporting electrolyte. The $A_r$ parameter may be used directly for the dilution titration analysis but use of the normalized $A_r/A_r(0)$ parameter tends to minimize measurement errors associated with changes in the electrode surface, background bath composition, and temperature. The suppressor concentration in the plating bath is determined from the volume fraction of plating bath required to decrease $A_r/A_r(0)$ or $A_r$ to a predetermined endpoint value, which may be a numerical value or a minimum value corresponding to substantially maximum suppression. The suppressor concentration in the plating bath is calculated by reference to the concentration of suppressor required to attain the $A_r/A_r(0)$ or $A_r$ titration endpoint value in a calibration run involving standard additions of the suppressor additive to the supporting electrolyte. In the alternative response curve analysis, the suppressor concentration is determined from the $A_r/A_r(0)$ or $A_r$ value for a measurement solution (supporting electrolyte plus a known volume fraction of plating bath sample) by interpolation with respect to an appropriate calibration curve. The effects of the anti-suppressor and leveler additives on the suppressor analysis are typically small but can be taken into account by utilizing a supporting electrolyte containing the concentrations of these additives measured or estimated to be present in the plating bath being analyzed.

For analysis of the anti-suppressor additive by the modified linear approximation technique (MLAT), the CVS rate parameter $A_r$ is first measured in a supporting electrolyte containing no anti-suppressor but with a sufficient amount of suppressor species added to substantially saturate suppression of the copper deposition rate. A predetermined volume ratio of the plating bath sample to be analyzed is then added to this fully-suppressed supporting electrolyte and $A_r$ is again measured. The $A_r$ measurement is then repeated in this measurement solution (supporting electrolyte plus a known volume fraction of the plating bath) after each addition (typically two) of known amounts of the anti-suppressor additive only. The concentration of the anti-suppressor in the plating bath sample is calculated assuming that $A_r$ varies linearly with anti-suppressor concentration, which is verified if the change in $A_r$ produced by standard additions of the same amount of anti-suppressor are equivalent.

In practice, the suppressor and anti-suppressor analyses are performed using the same electrochemical cell, and it has generally been deemed necessary to thoroughly clean and rinse the cell between these analyses to avoid cross-contamination errors. Residual organic additive species are a particular cross-contamination concern since such species strongly affect copper electrodeposition rate measurements, which are the basis for all CVS analyses. The cleaning and rinsing operations consume substantial amounts of both time and expensive chemicals, and generate significant quantities of hazardous wastes. These are especially serious issues for Damascene plating bath analyses, which must be performed frequently to attain consistent bottom-up filling and high product yields.

SUMMARY OF THE INVENTION

The present invention provides an integrated method for voltammetric analysis of a suppressor additive and an anti-suppressor additive in a plating bath. This method avoids the need to clean and rinse the analysis cell between the two analyses. In this method, the suppressor analysis is performed first, wherein the suppressor concentration in the plating bath is determined from the decrease in the metal electrodeposition rate in a plating bath supporting electrolyte produced by standard addition of the plating bath to the supporting electrolyte. The preferred supporting electrolyte has the same inorganic composition as the plating bath but contains no organic additives. Sufficient suppressor is added to the supporting electrolyte (via standard addition of the plating bath, suppressor additive, or combinations thereof) to provide a fully-suppressed measurement solution for which the electrodeposition rate of the metal is substantially the minimum value. The fully-suppressed measurement solution is then used as the background electrolyte for the anti-suppressor analysis, wherein the metal electrodeposition rate is measured in the fully-suppressed measurement solution before and after at least one standard addition of the anti-suppressor additive to the fully-suppressed measurement solution. The method is suitable for analysis of acid copper sulfate baths but could be applied to analysis of suppressor and anti-suppressor additives in other plating baths.

In a preferred embodiment, the metal electrodeposition rate is measured by the CVS method. The suppressor concentration may be determined by CVS response curve analysis or dilution titration analysis, for example, and the anti-suppressor concentration may be determined by the CVS linear approximation technique (LAT) or modified linear approximation technique (MLAT), for example. Preferably, sufficient suppressor additive is added to the measurement solution after the suppressor analysis to increase the overall suppressor concentration in the measurement solution to a predetermined value corresponding to substantially full suppression of the metal deposition rate. Alternatively, standard additions of the plating bath to the measurement solution may be continued until full suppression of the metal electrodeposition rate is attained.

The integrated CVS analysis of the present invention provides results comparable to those obtained with cell cleaning between the suppressor and anti-suppressor analyses, while significantly reducing the analysis time, consumption of expensive chemicals, and quantity of hazardous waste generated. The reduced analysis time enables closer process control, and the reductions in chemical consumption and waste generation save money and benefit the environment.

Further features and advantages of the invention will be apparent to those skilled in the art from the following detailed description, taken together with the accompanying drawings.

DETAILED DESCRIPTION OF THE INVENTION

Figure 1:
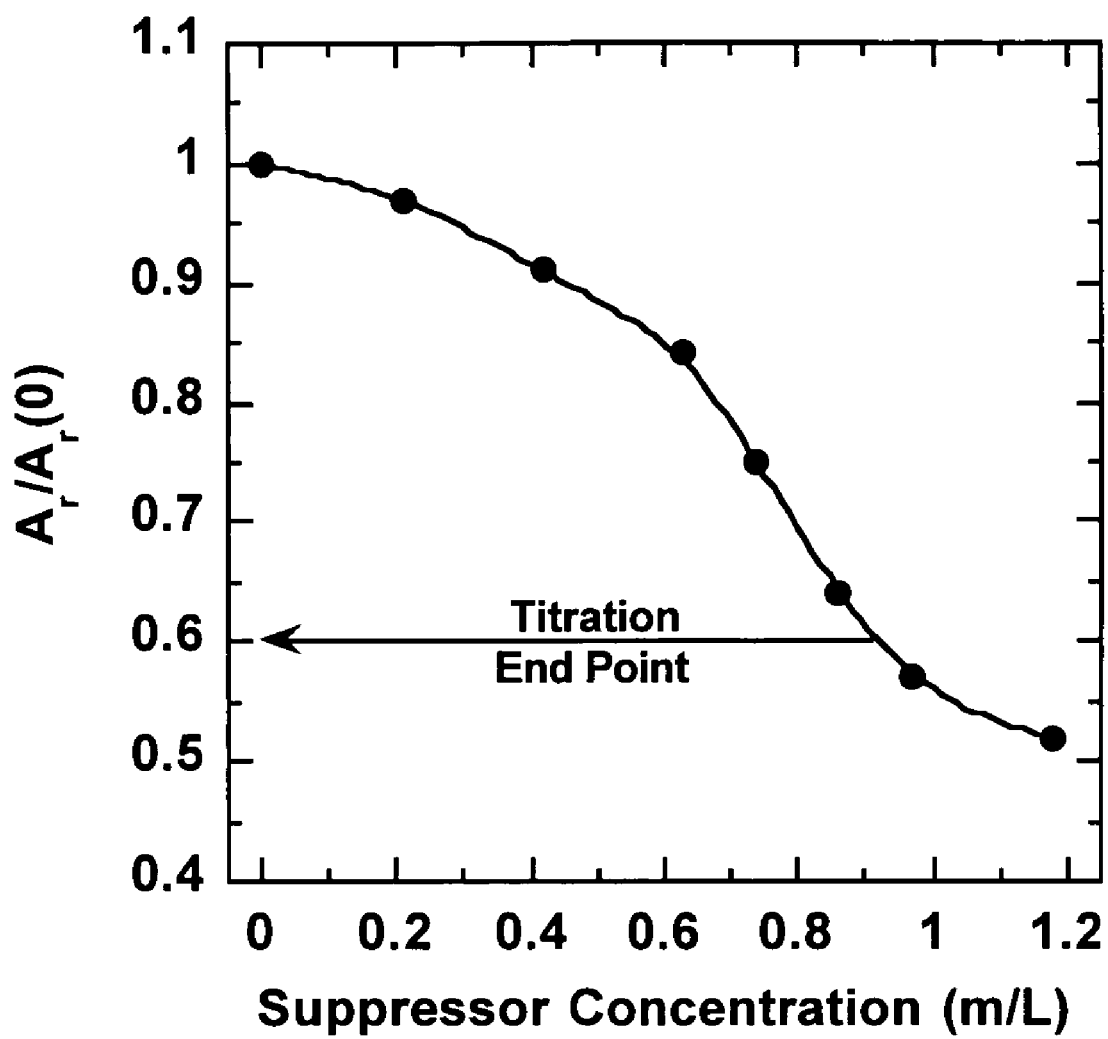
FIG. 1 shows a dilution titration plot of the CVS rate parameter $A_r/A_s(0)$ for the supporting electrolyte of a commercial acid copper plating bath vs. volume fraction of suppressor additive.

Technical terms used in this document are generally known to those skilled in the art. The term "electrode potential", or simply "potential", refers to the voltage occurring across a single electrode-electrolyte interface. In practice, the electrode potential often includes an appreciable resistive voltage drop in the electrolyte, which typically remains constant and does not affect voltammetric analysis results.

As used in this document, the terms "electroplating", "plating" and "electrodeposition" refer to metal electrodeposition and are equivalent. A "plating bath" contains organic additives whose concentrations are controlled within ranges, whereas the corresponding "supporting electrolyte" typically has substantially the same inorganic composition as the plating bath but no organic additives. In some cases, a supporting electrolyte may contain one or more organic additives at predetermined concentrations, or have an inorganic composition that differs from that of the plating bath. A "measurement solution" is a supporting electrolyte to which one or more standard additions of a plating bath or an additive have been made. The term "plating solution" is generic, encompassing all types of solutions used for metal electrodeposition. The symbol "M" means molar concentration.

In this document, the term "standard addition" generally means addition of a predetermined volume of a plating bath sample or of a standard additive solution to a predetermined volume of a supporting electrolyte or a measurement solution. The "volume fraction" is the volume of added plating bath sample or additive solution divided by the total volume of the solution after the addition. The term "standard addition" also encompasses addition of a known weight of a solid additive species to a known volume of a supporting electrolyte or a measurement solution. Calibration data are typically handled as calibration curves or plots but such data may be tabulated and used directly, especially by a computer, and the terms "curve" or "plot" include tabulated data.

Voltammetric data may be generated by scanning the electrode potential at a constant rate or by stepping the potential, or by a combination of potential scanning and stepping. A "cyclic voltammogram" is a plot of current or current density (on the y-axis) versus the working electrode potential (on the x-axis) typically obtained by cycling the working electrode potential with time between fixed negative and positive limits. A "potentiostat" is an electronic device for controlling the potential of a working electrode by passing current between the working electrode and a counter electrode so as to drive the working electrode to a desired potential relative to a reference electrode. Use of a potentiostat avoids passing appreciable current through the reference electrode, which might change its potential. Operation in the three-electrode mode may also reduce errors in the electrode potential associated with the resistive voltage drop in the electrolyte.

The present invention provides an integrated method for voltammetric analysis of a suppressor and an anti-suppressor additive in a plating bath that avoids the need to clean and rinse the analysis cell between the two analyses. In this method, the suppressor analysis is performed first, wherein the suppressor concentration in the plating bath under analysis is determined from the decrease in the metal electrodeposition rate produced by standard addition of the plating bath to a supporting electrolyte. A fully-suppressed measurement solution, for which the electrodeposition rate of the metal is substantially the minimum value, is provided by standard addition of the suppressor additive, the plating bath, or combinations thereof to the measurement solution resulting from the suppressor analysis. The fully-suppressed measurement solution is then used as the background electrolyte for the anti-suppressor analysis, wherein the metal electrodeposition rate is measured in the fully-suppressed measurement solution before and after at least one standard addition of the anti-suppressor additive to the fully-suppressed measurement solution. The suppressor concentration in the fully-suppressed measurement solution is preferably adjusted to a predetermined value so that variations in the metal electrodeposition rate due to differences in the suppressor concentration are avoided. Such variations are, however, typically small for the fully-suppressed measurement solution so that it may only be necessary to maintain the suppressor concentration within a range of concentrations corresponding to substantially full suppression.

The plating bath analysis method of the present invention comprises the following steps, which are preferably performed in the order specified. As those skilled in the art will appreciate, however, the order of some of the steps may be varied. The metal electrodeposition rate may be measured by a direct current (dc) or an alternating current (ac) method.

(1) measuring the electrodeposition rate of the metal in a supporting electrolyte of the plating bath under a first predetermined set of conditions. A preferred supporting electrolyte has the same inorganic composition as the plating bath being analyzed but contains no organic additives. The supporting electrolyte may, however, contain different inorganic constituents or different inorganic constituent concentrations than those in the plating bath if such compositional differences do not produce substantial changes in the metal electrodeposition rate as plating bath is added to the supporting electrolyte at the volume fractions used for the suppressor analysis. The supporting electrolyte may also contain one or more organic additives at predetermined concentrations. A leveler additive, for example, could be added to the supporting electrolyte at its concentration in the plating bath to minimize interference with the suppressor and anti-suppressor analyses. The metal electrodeposition rate is preferably measured by the CVS method using the metal stripping peak area at a predetermined electrode rotation rate ($A_r$) as the CVS rate parameter. In this case, variables that define the first predetermined set of conditions include the rotating electrode material and geometry, the electrode rotation rate, the potential scan rate and limits, and the solution temperature. This step provides a metal electrodeposition rate parameter for the supporting electrolyte, $A_r(0)$, for example, that may be used to normalize rate parameters from subsequent measurements to reduce measurement errors. A preferred normalized rate parameter is $A_r/A_r(0)$ but other normalized rate parameters could be used.

(2) providing a calibration curve by measuring the electrodeposition rate of the metal, under the first predetermined set of conditions, in a plurality of calibration solutions resulting from standard addition of the suppressor additive to the supporting electrolyte.

(3) measuring the electrodeposition rate of the metal, under the first predetermined set of conditions, in at least one measurement solution resulting from standard addition of the plating bath to the supporting electrolyte. A plurality of standard additions, as used in dilution titration analyses, is preferred but the suppressor concentration could be determined by response curve analysis using only one standard addition of the plating bath.

(4) determining the suppressor additive concentration in the plating bath from a decrease in the electrodeposition rate of the metal measured in Step (3) via reference to the calibration curve provided in Step (2). The suppressor concentration in the plating bath may be determined by CVS dilution titration analysis or CVS response curve analysis, for example. For the dilution titration analysis, the suppressor concentration is calculated based on the equivalence in the suppressor concentrations in the measurement solution and the calibration solution at the titration endpoint, which may be a predetermined value or substantially the minimum value for the CVS rate parameter. For the response curve analysis, the suppressor concentration is calculated by interpolation with respect to the calibration curve provided in Step (2). As known in the art, calculation of the suppressor concentration in the plating bath must take into account dilutions resulting from addition of bath samples and additive solutions to the measurement solution.

(5) providing a fully-suppressed measurement solution, for which the electrodeposition rate of the metal is substantially the minimum value, by standard addition of the suppressor additive, the plating bath, or combinations thereof to the final measurement solution from Step (3). Preferably, the suppressor concentration is first determined by standard additions of the plating bath to the supporting electrolyte using an endpoint at which the measurement solution is not fully suppressed, and a fully-suppressed measurement solution having a predetermined suppressor concentration is then provided by standard addition of suppressor additive to the measurement solution. Alternatively, plating bath may be added to the measurement solution until the measured metal electrodeposition rate is substantially a minimum, indicating substantially full suppression of the metal electrodeposition rate. In this case, the suppressor concentration can be calculated in an iterative process to provide a predetermined suppressor concentration but the anti-suppressor concentration in the measurement solution resulting from plating bath standard additions cannot readily be varied to improve measurement precision.

(6) measuring the electrodeposition rate of the metal in the fully-suppressed measurement solution under a second predetermined set of conditions before and after at least one standard addition of the anti-suppressor additive to the fully-suppressed measurement solution provided in Step (5). The first predetermined set of conditions and the second predetermined set of conditions may be the same conditions or different conditions. The CVS linear approximation technique (LAT) or modified linear approximation technique (MLAT) may be used, for example. A plurality of anti-suppressor standard additions, typically two, is typically used to improve the measurement precision.

(7) determining the anti-suppressor additive concentration in the copper plating bath from an increase in the copper electrodeposition rate measured in Step (6). The anti-suppressor concentration may be determined by the CVS linear approximation technique (LAT) or modified linear approximation technique (MLAT), for example.

The method of the present invention is suitable for analysis of acid copper plating baths. Acid copper sulfate is the most widely used acid copper bath but the method of the present invention may also be applied to acid copper baths employing a variety of anions, including sulfate, chloride, bromide, iodide, fluoroborate, sulfamate, alkylsulfonate, and mixtures thereof. In addition, the method could be applied to analysis of suppressor and anti-suppressor additives in plating baths used to electrodeposit other metals (tin, tin-lead, nickel or cobalt, for example).

The metal deposition rate for the method of the present invention is preferably determined by cyclic voltammetric stripping (CVS) or cyclic pulse voltammetric stripping (CPVS). As used in this document, the term "cyclic voltammetric stripping" or "CVS" implicitly includes the CPVS method, which is a variation of the CVS method. Likewise, the term "CVS rate parameter" includes the analogous CPVS voltammetric rate parameters.

In the CVS method, the potential of an inert working electrode, typically platinum, is cycled in a plating solution at a constant rate between fixed potential limits so that a metal is alternately electrodeposited on the electrode surface and anodically stripped back into the solution. Preferably, a rotating disk electrode configuration is used for the working electrode to control solution mass transport so as to improve the sensitivity and reproducibility of the analysis results. The metal deposition rate is preferably measured via the metal stripping peak area at a constant electrode rotation rate ($A_r$) but may also be determined from the stripping peak height, or from the electrode impedance, current (including average current), or integrated current (i.e., charge) measured for a predetermined cathodic potential or potential range (with or without electrode rotation). All of these rate parameters provide a relative measure of the metal electrodeposition rate that can readily be used for comparisons only when the measurement conditions are the same for a given analysis. Improved reproducibility and accuracy may be provided by using a normalized rate parameter, for example, $A_r/A_r(0)$, which is the ratio of the CVS stripping peak area for a measurement solution to that for the supporting electrolyte.

For CVS analyses, a plurality of potential cycles is typically employed to condition the working electrode surface so as to provide reproducible results. In this case, data are accepted only when a steady-state condition is reached, as indicated by substantially equivalent voltammograms or voltammetric features on successive cycles. Typically, steady state is indicated by successive $A_r$ values that differ by less than a predetermined percentage (0.5%, for example).

The inert working electrode for CVS measurements may be comprised of any suitable electrically conducting material that is stable in the plating solution under the conditions used for the voltammetric analysis, but is preferably comprised of a noble metal, for example, platinum, iridium, gold, osmium, palladium, rhenium, rhodium, ruthenium, and alloys thereof. Other oxidation-resistant metals and alloys, stainless steel, for example, might also be used as working electrode materials. A typical CVS rotating disk electrode is comprised of a platinum metal disk (3–5 mm diameter), with an electrical contact wire on the backside, embedded flush with one end of an insulating plastic cylinder (10–20 mm diameter). The rotating disk electrode may be fabricated by press fitting the metal disk into a hole in the plastic but is preferably fabricated by hot pressing, which forms a seal between the metal and the plastic that prevents intrusion of the solution. A suitable plastic for mounting rotating disk electrodes by hot pressing is polytrifluorochloroethylene (Kel-F®). The rotating disk electrode is usually rotated at a constant rate (100–10,000 rpm) but the electrode rotation may be modulated with time.

Precise control over the working electrode potential needed for CVS measurements is typically provided via an electronic potentiostat in conjunction with a counter electrode and a reference electrode, e.g., silver-silver chloride (SSCE), mercury-mercury sulfate, or saturated calomel electrode (SCE). A double junction may be used to extend the life of the reference electrode by inhibiting intrusion of plating bath species. The counter electrode may be a reactive metal (copper or a copper alloy, for example) or an inert metal. Depolarizers (sulfur or phosphorus, for example) may be included in the counter electrode to facilitate dissolution of the metal so as to avoid breakdown of the plating solution. Practically any electrical conductor that resists oxidation and reduction in the plating solution may be used as an inert counter electrode, including metals, alloys and conducting oxides (mixed titanium-ruthenium oxide, for example). A preferred inert counter electrode material is 316 stainless steel, which is highly oxidation-resistant and relatively inexpensive but other types of stainless steel or other oxidation-resistant alloys (Inconel, for example) may also be used. Other suitable inert counter electrode materials include noble metals, for example, platinum, iridium, gold, osmium, palladium, rhenium, rhodium, ruthenium, and alloys thereof.

Metal deposition rates according to the present invention may also be measured by methods other than CVS, including those based on measurements of the ac impedance of the cathode, for example. The same electrode materials and configurations can be used for such alternative methods. Although the precision and reproducibility of the analysis might be degraded, current measurements reflecting the metal deposition rate could also be made at a stationary electrode and/or without potential cycling. If a stationary working electrode is used for one or both of the suppressor and anti-suppressor analyses of the present invention, the hydrodynamic conditions at the electrode surface are preferably controlled, by stirring or pumping the solution, for example.

The composition of acid copper electroplating baths varies greatly depending on the type of bath and the supplier. High-acid baths typically contain 40–100 g/L copper sulfate, 140–240 g/L sulfuric acid and 25–100 ppm chloride ion. Low-acid baths typically contain 125–200 g/L copper sulfate, 1–40 g/L sulfuric acid and 25–100 ppm chloride ion. Acid copper plating bath additives are generally proprietary formulations supplied in the form of solutions that may contain more than one additive species or combination of additives. The chemical nature and concentrations of the additive species are typically not specified and may be changed from time to time by the supplier without notice.

Since chloride exerts a strong effect on the functioning of suppressor additives used in acid copper baths, its concentration should, if necessary, be adjusted to be within the appropriate range (typically, 25 to 100 ppm) in the plating bath sample being analyzed, and in the supporting electrolyte used for the analysis. Variations in the chloride, sulfuric acid and copper ion concentrations within the ranges recommended by the bath supplier usually have a negligible effect on the suppressor and anti-suppressor analysis results and typically need to be adjusted in measurement solutions only for analyses requiring very high accuracy.

Copper electrodeposition rate measurements are preferably made at a constant temperature (within ±0.5° C.) since errors resulting from temperature variations may be significant. Acid copper baths are typically operated at ambient temperature but measurements may be made at a higher or a lower temperature. The accuracy of CVS rate parameter measurements may be improved by employing a slightly elevated solution temperature (3° or 4° C. above room temperature, for example) that can be more consistently maintained.

Best results for the analysis of the present invention are provided by optimizing the CVS measurement parameters for the particular bath type and additive system employed. The key CVS measurement parameters and their typical ranges for acid copper baths include the electrode rotation rate (100–10,000 rpm), potential scan rate (10–1000 mV/s), negative potential limit (−0.05 to −0.5 V vs. SSCE) and positive potential limit (1.4 to 1.8 V vs. SSCE). A positive potential limit of relatively high voltage (in the oxygen evolution region) is typically used so that organic species adsorbed on the electrode surface are removed by electrochemical oxidation on each cycle, which provides more reproducible results. Additional CPVS measurement parameters include the potentials and hold times for the pulses or steps used.

Optimization of the CVS measurement parameters typically involve variations in the negative potential limit and/or the potential scan rate, which determine the amount of metal deposited on the electrode and thus the sensitivity of the rate parameter to additive effects. For example, a more negative potential limit or slower scan rate may be needed to deposit sufficient metal for the suppressor analysis when the suppressor effect is relatively strong. The potential scan rate and limits also influence the sensitivity of the rate parameter to additives by affecting additive adsorption/desorption processes, as well as the relative magnitudes of charging and faradaic currents. Another key optimization parameter is the electrode rotation rate, which determines the rate at which additive species are replenished at the electrode surface as they are consumed during metal electrodeposition. Typically, the rotation rate is increased for detection of an additive species present at relatively low concentration.

DESCRIPTION OF A PREFERRED EMBODIMENT

A preferred approach for analysis of acid copper baths according to the present invention is to utilize CVS procedures based on measurements of the integrated copper stripping peak area ($A_r$) for a Pt disk electrode rotating at a constant rate. A preferred procedure is to first determine the suppressor concentration in the plating bath by CVS dilution titration, wherein $A_r(0)$ is first measured for the plating bath supporting electrolyte and $A_r$ values are then measured for a plurality of measurement solutions resulting from standard addition of the plating bath to the supporting electrolyte. The suppressor concentration in the plating bath is preferably determined from the volume fraction of plating bath required to decrease $A_r/A_r(0)$ to a predetermined value (typically in the 0.4 to 0.6 range), which serves as the endpoint for the dilution titration. The suppressor concentration in the plating bath is calculated by reference to the suppressor concentration corresponding to the titration endpoint, which is determined from a calibration curve of $A_r/A_r(0)$ vs. suppressor additive concentration generated by standard additions of the suppressor additive to the supporting electrolyte. A fully-suppressed measurement solution is then provided, preferably, by standard addition of the suppressor additive to the measurement solution resulting from the suppressor analysis. The total suppressor concentration in the fully-suppressed measurement solution, resulting from standard additions of the plating bath and the suppressor additive, is preferably a predetermined value. The anti-suppressor concentration in the plating bath is preferably determined via MLAT analysis by measuring $A_r$ in the fully-suppressed measurement solution before and after at least one standard addition of the anti-suppressor additive solution. Two standard additions of anti-suppressor additive are preferred. The concentration of anti-suppressor in the plating bath sample is calculated by assuming a linear $A_r$ response to the anti-suppressor (in the fully-suppressed measurement solution) resulting from standard additions of both the plating bath and the anti-suppressor additive.

A preferred procedure for CVS voltammetric measurements is to cycle the potential of a rotating platinum disk electrode relative to a reference electrode between fixed positive and negative potential limits via a potentiostat and a counter electrode. Measurements are preferably made at a constant temperature (within ±0.5° C.). The concentrations of chloride and additives other than the suppressor and anti-suppressor in the plating bath are preferably maintained within the ranges recommended by the bath supplier (for chloride ion, typically 25 to 100 ppm). After each standard addition, sufficient time should be allowed for stirring via the rotating disk electrode (or other means) to provide a homogeneous solution.

Prior to the dilution titration analysis, the potential of the working electrode is preferably cycled (over the potential range used for the analysis) in the plating solution to condition the electrode surface. For both the electrode conditioning and the dilution titration analysis, the potential of the working electrode is preferably cycled until successive $A_r$ values differ by less than a predetermined percentage (typically 0.5%).

Optimum CVS measurement parameters for the method of the present invention depend on the type of acid copper plating bath and the specific additive system. For the suppressor analysis, the negative potential limit may be any value more negative than −0.15 V vs. SSCE but the preferred value is typically between −0.35 and −0.45 V vs. SSCE. The same limits may be used for the anti-suppressor analysis. Typical ranges for other CVS parameters are 100–5000 rpm for the electrode rotation rate, 50–500 mV/s for the potential scan rate, and 1.4 to 1.8 V vs. SSCE for the positive potential limit.

The efficacy of the present invention was demonstrated via CVS dilution titration and MLAT analyses of a commercial acid copper plating bath (Enthone LAVF) employing a suppressor additive, an anti-suppressor additive, and a leveling additive. The supplier uses the term "accelerator" for the anti-suppressor additive in this bath. The analyses were performed using a QLC-7000 automatic plating bath analyzer (ECI Technology, Inc.). The target supporting electrolyte contained 75 g/L $CuSO_4 \cdot 5H_2O$, 175 g/L $H_2SO_4$, and 50 mg/L chloride ion (added as hydrochloric acid). The CVS rate parameter was the copper stripping peak area ($A_r$) measured at 25° C. using a 4-mm diameter platinum rotating disk electrode (2500 rpm) cycled between −0.225 V and +1.575 V vs. SSCE/M (silver-silver chloride electrode modified by replacing the solution in a standard SSCE electrode with a saturated AgCl solution also containing 0.1 $\underline{M}$ KCl and 10 volume % sulfuric acid). For $A_r$ measurements, the anodic current was integrated over the potential range from the zero-current potential (at the cathodic-anodic crossover) to 0.55 V vs. SSCE/M. The potential scan rate was 300 mV/s for the suppressor analysis and 200 mV/s for the accelerator analysis. The counter electrode was a stainless steel rod.

FIG. 1 shows a calibration curve of $A_r/A_r(0)$ vs. suppressor concentration in the supporting electrolyte. An $A_r/A_r(0)$ value of 0.60 was used as the endpoint for the dilution titration analyses, which were continued until an $A_r/A_r(0)$ value of about 0.55 was attained. The suppressor concentration in the plating bath was calculated from the volume fraction of the plating bath in the supporting electrolyte at the endpoint in the titration.

Figure 2:
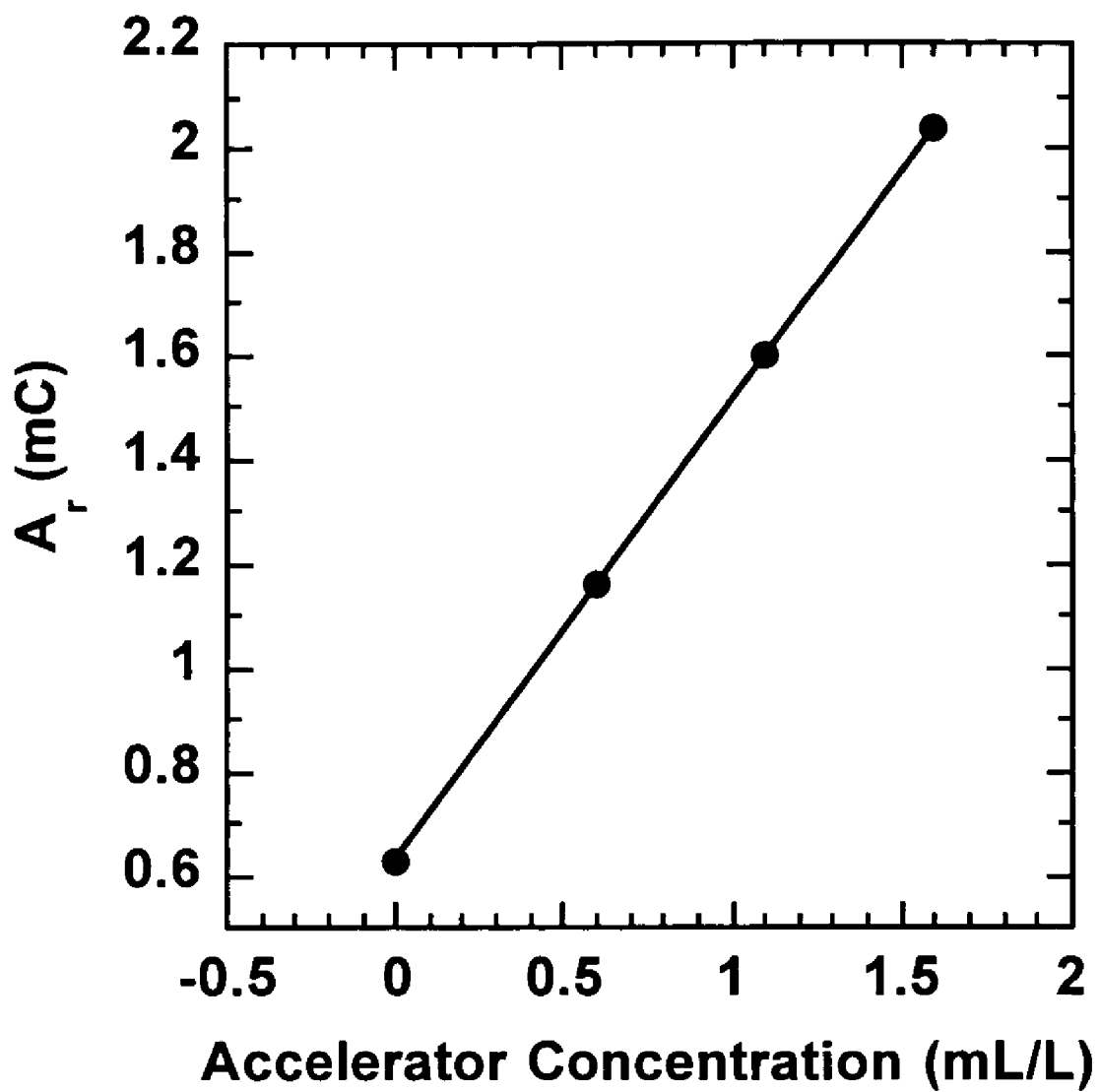
FIG. 2 shows a plot of $A_r$ for a fully-suppressed supporting electrolyte of a commercial acid copper bath vs. volume fraction of anti-suppressor (accelerator) additive.

FIG. 2 illustrates the linear dependence of $A_r$ measured in the fully-suppressed supporting electrolyte (50 mL/L suppressor additive) on the accelerator additive concentration, which is the basis for the MLAT anti-suppressor analysis. The accelerator concentration was determined from the y-axis intercept assuming a linear dependence of $A_r$ on the accelerator concentration.

For comparison, this commercial acid copper bath was analyzed by the standard method of cleaning and rinsing the cell between the suppressor and anti-suppressor analyses, and by the method of the present invention whereby the measurement solution from the suppressor analysis is used for the anti-suppressor analysis. Before measurements were begun, the syringes used for both the suppressor and accelerator analysis were primed. For the analysis according to the present invention, the concentration of the suppressor additive in the plating bath was first determined by dilution titration analysis. The suppressor concentration in the resulting measurement solution was then adjusted to 50 mL/L by addition of suppressor additive solution. The concentration of the accelerator in the plating bath was then determined by MLAT analysis using two 0.5 mL/L standard additions of the accelerator additive. As part of the overall analysis, the concentrations of leveler additive, copper ion, sulfuric acid and chloride were also measured by standard methods. Ten complete analyses were performed about 3 hours apart.

Tables 1a and 2a show the results of the analyses according to the prior art for baths containing relatively high and low concentrations of the bath constituents, and Table 1b and 2b show the results of the analyses for the same baths according to the present invention. The accuracy and precision provided by the prior art method and the method of the invention are comparable for all bath constituents. Similar results were obtained for the target electrolyte.

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

TABLE 1a

Standard Analyses According to the Prior Art of an Acid Copper Bath with Low Constituent Concentrations

| Time Frame (Minutes) | Suppressor (mL/L) | Accelerator (mL/L) | Leveler (mL/L) | Copper (g/L) | Acid (g/L) | Chloride (mg/L) |
|---|---|---|---|---|---|---|
| 0–19 | 1.47 | 3.79 | 1.53 | 35.0 | 7.94 | 40.4 |
| 160–179 | 1.47 | 3.78 | 1.53 | 34.4 | 7.98 | 40.6 |

TABLE 1a-continued

Standard Analyses According to the Prior Art of an
Acid Copper Bath with Low Constituent Concentrations

| Time Frame (Minutes) | Suppressor (mL/L) | Accelerator (mL/L) | Leveler (mL/L) | Copper (g/L) | Acid (g/L) | Chloride (mg/L) |
|---|---|---|---|---|---|---|
| 333–352 | 1.48 | 3.83 | 1.53 | 34.8 | 8.1 | 40.4 |
| 494–512 | 1.49 | 3.83 | 1.47 | 34.9 | 8.09 | 40.5 |
| 653–671 | 1.47 | 3.82 | 1.47 | 34.8 | 8.18 | 40.3 |
| 812–831 | 1.47 | 3.8 | 1.46 | 34.9 | 8.09 | 40.4 |
| 971–990 | 1.47 | 3.85 | 1.42 | 34.9 | 8.13 | 40.5 |
| 1175–1194 | 1.47 | 3.88 | 1.53 | 34.7 | 8.06 | 40.5 |
| 1336–1354 | 1.45 | 3.88 | 1.51 | 35.0 | 8.14 | 40.5 |
| 1508–1527 | 1.48 | 3.85 | 1.52 | 34.9 | 8.16 | 40.4 |
| Expected | 1.50 | 4.00 | 1.50 | 35.0 | 8.00 | 40.0 |
| Average | 1.47 | 3.83 | 1.50 | 34.8 | 8.09 | 40.5 |
| Accuracy (%) | 1.87 | 4.22 | 0.20 | 0.49 | 1.09 | 1.15 |
| Std. Deviation | 0.01 | 0.03 | 0.04 | 0.16 | 0.08 | 0.10 |
| Rel. Std. Dev. (%) | 0.70 | 0.91 | 2.62 | 0.45 | 0.95 | 0.24 |

TABLE 1b

Analyses According to the Present Invention of an
Acid Copper Bath with Low Constituent Concentrations

| Time Frame (Minutes) | Suppressor (mL/L) | Accelerator (mL/L) | Leveler (mL/L) | Copper (g/L) | Acid (g/L) | Chloride (mg/L) |
|---|---|---|---|---|---|---|
| 0–21 | 1.53 | 4.14 | 1.59 | 35.1 | 8.12 | 40.1 |
| 177–199 | 1.53 | 4.08 | 1.61 | 35.1 | 8.16 | 40.1 |
| 355–376 | 1.62 | 4.15 | 1.61 | 35.1 | 8.13 | 40.2 |
| 533–555 | 1.53 | 4.15 | 1.63 | 35.1 | 8.17 | 40.3 |
| 744–765 | 1.47 | 4.15 | 1.59 | 34.9 | 8.06 | 40.1 |
| 943–965 | 1.48 | 4.06 | 1.61 | 35.1 | 8.06 | 40.2 |
| 1122–1144 | 1.51 | 4.14 | 1.53 | 35.1 | 8.08 | 40.4 |
| 1302–1324 | 1.49 | 4.11 | 1.48 | 34.9 | 8.06 | 40.3 |
| 1482–1504 | 1.5 | 4.08 | 1.52 | 35.1 | 8.41 | 39.7 |
| 1541–1563 | 1.5 | 4.09 | 1.52 | 34.9 | 8.07 | 39.8 |
| Expected | 1.50 | 4.00 | 1.50 | 35.0 | 8.00 | 40.0 |
| Average | 1.52 | 4.12 | 1.57 | 35.0 | 8.13 | 40.1 |
| Accuracy (%) | 1.07 | 2.88 | 4.60 | 0.12 | 1.65 | 0.30 |
| Std. Deviation | 0.04 | 0.04 | 0.05 | 0.09 | 0.11 | 0.21 |
| Rel. Std. Dev. (%) | 2.78 | 0.85 | 3.28 | 0.27 | 1.31 | 0.51 |

TABLE 2a

Standard Analyses According to the Prior Art of an
Acid Copper Bath with High Constituent Concentrations

| Time Frame (Minutes) | Suppressor (mL/L) | Accelerator (mL/L) | Leveler (mL/L) | Copper (g/L) | Acid (g/L) | Chloride (mg/L) |
|---|---|---|---|---|---|---|
| 0–17 | 2.47 | 7.59 | 3.46 | 44.7 | 12.0 | 60.9 |
| 160–190 | 2.47 | 7.59 | 3.43 | 44.6 | 11.9 | 60.7 |
| 333–351 | 2.46 | 7.67 | 3.42 | 44.8 | 12.2 | 60.8 |
| 483–511 | 2.39 | 7.77 | 3.37 | 44.7 | 12.3 | 61.0 |
| 652–670 | 2.36 | 7.78 | 3.35 | 44.6 | 12.4 | 60.6 |
| 811–829 | 2.43 | 7.73 | 3.38 | 44.7 | 12.2 | 61.1 |
| 971–989 | 2.3 | 7.77 | 3.27 | 44.6 | 12.2 | 60.7 |
| 1175–1193 | 2.4 | 7.76 | 3.43 | 44.6 | 12.2 | 60.7 |
| 1337–1354 | 2.33 | 7.8 | 3.4 | 44.7 | 12.5 | 60.9 |
| 1509–1526 | 2.38 | 7.72 | 3.4 | 44.8 | 12.3 | 60.9 |
| Expected | 2.50 | 8.00 | 3.50 | 45.0 | 12.0 | 60.0 |
| Average | 2.40 | 7.72 | 3.39 | 44.7 | 12.2 | 60.8 |
| Accuracy (%) | 3.99 | 3.53 | 3.11 | 0.71 | 1.94 | 1.36 |
| Std. Deviation | 0.06 | 0.08 | 0.05 | 0.07 | 0.17 | 0.16 |
| Rel. Std. Dev. (%) | 2.45 | 0.99 | 1.58 | 0.16 | 1.38 | 0.26 |

TABLE 2b

Analyses According to the Present Invention of an
Acid Copper Bath with Low Constituent Concentrations

| Time Frame (Minutes) | Suppressor (mL/L) | Accelerator (mL/L) | Leveler (mL/L) | Copper (g/L) | Acid (g/L) | Chloride (mg/L) |
|---|---|---|---|---|---|---|
| 0–21 | 2.53 | 8.14 | 3.46 | 45.0 | 12.2 | 60.4 |
| 178–198 | 2.51 | 8.28 | 3.47 | 44.9 | 12.2 | 60.1 |
| 355–376 | 2.5 | 8.17 | 3.47 | 45.0 | 12.2 | 60.5 |
| 535–556 | 2.52 | 8.28 | 3.47 | 45.0 | 12.0 | 60.3 |
| 745–766 | 2.43 | 8.2 | 3.44 | 44.9 | 12.0 | 60.3 |
| 945–965 | 2.46 | 8.26 | 3.35 | 45.0 | 12.1 | 60.3 |
| 1124–1145 | 2.52 | 8.22 | 3.36 | 45.0 | 12.1 | 60.6 |
| 1304–1325 | 2.49 | 8.16 | 3.4 | 44.9 | 12.2 | 60.7 |
| 1483–1504 | 2.48 | 8.11 | 3.38 | 44.9 | 12.1 | 59.7 |
| 1663–1684 | 2.41 | 8.2 | 3.25 | 44.9 | 12.2 | 60.1 |
| Expected | 2.50 | 8.00 | 3.50 | 45.0 | 12.0 | 60.0 |
| Average | 2.49 | 8.20 | 3.41 | 44.9 | 12.1 | 60.3 |
| Accuracy (%) | 0.60 | 2.53 | 2.71 | 0.12 | 1.05 | 0.49 |
| Std. Deviation | 0.04 | 0.06 | 0.07 | 0.05 | 0.07 | 0.30 |
| Rel. Std. Dev. (%) | 1.62 | 0.72 | 2.11 | 0.12 | 0.59 | 0.49 |

We claim:

1. A method for measuring the concentrations of a suppressor additive and an anti-suppressor additive in a plating bath for electrodeposition of a metal, comprising the steps of:

(1) measuring the electrodeposition rate of the metal in a supporting electrolyte of the plating bath under a first predetermined set of conditions;

(2) providing a calibration curve by measuring the electrodeposition rate of the metal, under the first predetermined set of conditions, in a plurality of calibration solutions resulting from standard addition of the suppressor additive to the supporting electrolyte;

(3) measuring the electrodeposition rate of the metal, under the first predetermined set of conditions, in at least one measurement solution resulting from standard addition of the plating bath to the supporting electrolyte;

(4) determining the suppressor additive concentration in the plating bath from a decrease in the electrodeposition rate of the metal measured in Step (3) via reference to the calibration curve provided in Step (2);

(5) providing a fully-suppressed measurement solution, for which the electrodeposition rate of the metal is substantially the minimum value, by standard addition of the suppressor additive, the plating bath, or combinations thereof to the final measurement solution from Step (3);

(6) measuring the electrodeposition rate of the metal in the fully-suppressed measurement solution under a second predetermined set of conditions before and after at least one standard addition of the anti-suppressor additive to the fully-suppressed measurement solution provided in Step (5); and (7) determining the anti-suppressor additive concentration in the plating bath from an increase in the electrodeposition rate of the metal measured in Step (6).

2. The method of claim 1, wherein the plating bath is an acid copper plating bath comprising anions selected from the group consisting of sulfate, chloride, bromide, iodide, fluoroborate, sulfamate, alkylsulfonate, and mixtures thereof.

3. The method of claim 1, wherein the supporting electrolyte contains at least one organic additive.

4. The method claim 1, wherein the metal electrodeposition rate is measured via an electrodeposition rate parameter determined by a CVS method.

5. The method of claim 4, wherein the electrodeposition rate parameter is selected from the group consisting of metal stripping peak area, metal stripping peak height, current at a predetermined cathodic potential, integrated current over a predetermined cathodic potential range, and average current over a predetermined cathodic potential range.

6. The method of claim 1, wherein the metal electrodeposition rate is measured by an alternating current (ac) method.

7. The method of claim 1, wherein the first predetermined set of conditions and the second predetermined set of conditions are the same set of conditions.

8. A method for measuring the concentrations of a suppressor additive and an anti-suppressor additive in an acid copper plating bath, comprising the steps of:

(1) measuring the copper electrodeposition rate in a supporting electrolyte of the copper plating bath under a first predetermined set of conditions;

(2) providing a calibration curve by measuring the copper electrodeposition, under the first predetermined set of conditions, in a plurality of calibration solutions resulting from standard addition of the suppressor additive to the supporting electrolyte;

(3) measuring the copper electrodeposition rate, under the first predetermined set of conditions, in at least one measurement solution resulting from standard addition of the acid copper plating bath to the supporting electrolyte;

(4) determining the suppressor additive concentration in the plating bath from a decrease in the copper electrodeposition rate measured in Step (3) via reference to the calibration curve provided in Step (2);

(5) providing a fully-suppressed copper measurement solution, for which the copper electrodeposition rate is substantially the minimum value, by standard addition of the suppressor additive, the copper plating bath, or combinations thereof to the final copper measurement solution from Step (3);

(6) measuring the copper electrodeposition rate in the fully-suppressed copper measurement solution under a second predetermined set of conditions before and after at least one standard addition of the anti-suppressor additive to the fully-suppressed copper measurement solution provided in Step (5); and (7) determining the anti-suppressor additive concentration in the copper plating bath from an increase in the copper electrodeposition rate measured in Step (6).

9. The method of claim 8, wherein the acid copper plating bath comprises anions selected from the group consisting of sulfate, chloride, bromide, iodide, fluoroborate, sulfamate, alkylsulfonate, and mixtures thereof.

10. The method of claim 8, wherein the supporting electrolyte contains at least one organic additive.

11. The method claim 8, wherein the copper electrodeposition rate is measured via an electrodeposition rate parameter determined by a CVS method.

12. The method of claim 11, wherein the electrodeposition rate parameter is selected from the group consisting of copper stripping peak area, copper stripping peak height, current at a predetermined cathodic potential, integrated current over a predetermined cathodic potential range, and average current over a predetermined cathodic potential range.

13. The method of claim 8, wherein the copper electrodeposition rate is measured by an alternating current (ac) method.

14. The method of claim 8, wherein the first predetermined set of conditions and the second predetermined set of conditions are the same set of conditions.

15. A method for measuring the concentrations of a suppressor additive and an anti-suppressor additive in an acid copper plating bath, comprising the steps of:

(1) determining the suppressor concentration in the acid copper plating bath by a first CVS method that includes the step of measuring a first CVS rate parameter in an acid copper supporting electrolyte before and after a plurality of standard additions of the acid copper plating bath to the acid copper supporting electrolyte;

(2) adding the suppressor additive, the acid copper plating bath, or combinations thereof to the acid copper measurement solution resulting from Step (1) to provide a fully-suppressed acid copper measurement solution with a predetermined concentration of the suppressor additive; and (3) determining the anti-suppressor additive concentration in the acid copper plating bath by a second CVS method that includes the step of measuring a second CVS rate parameter in the fully-suppressed acid copper measurement solution from Step (2) after at least one standard addition of the anti-suppressor additive.

16. The method of claim 15, wherein the acid copper plating bath comprises anions selected from the group consisting of sulfate, chloride, bromide, iodide, fluoroborate, sulfamate, alkylsulfonate, and mixtures thereof.

17. The method of claim 15, wherein the acid copper supporting electrolyte contains at least one organic additive.

18. The method of claim 15, wherein the first CVS method is selected from the group consisting of dilution titration analysis and response curve analysis.

19. The method of claim 15, wherein the second CVS method is selected from the group consisting of linear approximation technique (LAT) and modified linear approximation technique (MLAT).

20. The method of claim 15, wherein the first CVS rate parameter and the second CVS rate parameter are selected from the group consisting of copper stripping peak area, copper stripping peak height, current at a predetermined cathodic potential, integrated current over a predetermined cathodic potential range, and average current over a predetermined cathodic potential range.

* * * * *